(12) United States Patent
Park et al.

(10) Patent No.: US 7,875,287 B2
(45) Date of Patent: Jan. 25, 2011

(54) TC-LABELED ARYLPIPERAZINE DERIVATIVES FOR IMAGING SEROTONIN RECEPTOR

(75) Inventors: Sang Hyun Park, Daejeon (KR); Hue Jeong Kwon, Daejeon (KR); Seung Ho Jang, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 1385 days.

(21) Appl. No.: 11/272,585

(22) Filed: Nov. 10, 2005

(65) Prior Publication Data

US 2007/0036715 A1    Feb. 15, 2007

(30) Foreign Application Priority Data

Aug. 11, 2005  (KR) ...................... 10-2005-0073622

(51) Int. Cl.
*A61F 2/00*  (2006.01)
*A61K 51/00*  (2006.01)

(52) U.S. Cl. ...................... 424/426; 424/1.65; 546/227; 546/228

(58) Field of Classification Search ........................ None
See application file for complete search history.

(56) References Cited

U.S. PATENT DOCUMENTS 6,171,576 B1 *  1/2001  Meltzer et al. ............. 424/1.65

FOREIGN PATENT DOCUMENTS

KR    10-2000-0051075 A  *  8/2000

OTHER PUBLICATIONS

Hom et al.; Nuclear Medicine & Biology, vol. 24, pp. 485-498 (1997).*

Advanced Organic Chemistry 4th Ed. (1992); Jerry March; Ch. 10.*
Machine Translation of KR 1020000051075 (2 copies).*
Dirk Michalik, et al., A Short and Efficient Synthesis of N-Aryl-and-N-Heteroaryl-N'- . . . , Tetrahedron Letters, vol. 45, pp. 2057-2061, 2004.
G. Bormans, et al., Synthesis, Radio-LC-MS Analysis . . . , J. Label Compd. Radiopharm, vol. 46, pp. 575-585, 2003.
Bernard J. Cleynhens, et al., S-Trityl Protection of Bis-Amino Bis-Thiol . . . , Tetrahedron Letters, vol. 44, pp. 2597-2600, 2003.

* cited by examiner

*Primary Examiner*—Robert A Wax
*Assistant Examiner*—Jeffrey T Palenik
(74) *Attorney, Agent, or Firm*—Lucas & Mercanti, LLP (57) ABSTRACT

The present invention relates to Tc-labeled arylpiperazine derivatives for imaging serotonin receptor and, more particularly, to arylpiperazine derivatives coupled with MAMA-disulfide, $N_2S_2$ or dimethyl-$N_2S_2$ chelating ligand represented by the following chemical formula (1).

[Chemical Formula 1]

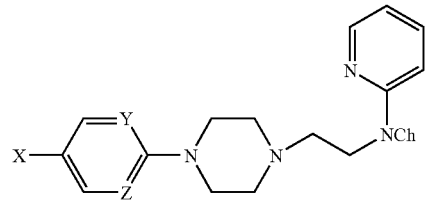

New arylpiperazine derivatives according to the present invention have no problem of amide hydrolysis in metabolism and have a high affinity for serotonin receptors, and can be labeled with an optimum radionuclide of technetium, thereby being usefully applied for monitoring neurodegenerative diseases or neurological diseases of a mammal.

17 Claims, 7 Drawing Sheets

TC-LABELED ARYLPIPERAZINE DERIVATIVES FOR IMAGING SEROTONIN RECEPTOR

This patent application claims th benefit of priority from Korean Patent Application No. 10-2005-0073622 filed Aug. 11, 2005, the contents of which are incorporated herein by reference

BACKGROUND OF THE INVENTION

1. Field of the Invention

The present invention relates to Tc-labeled arylpiperazine derivatives for imaging serotonin receptor, and more particularly, to arylpiperazine derivatives coupled with MAMA-disulfide, $N_2S_2$ or dimethyl-$N_2S_2$ chelating ligand, which is useful for imaging cranial nervous system.

2. Description of Prior Art

Transmission of nerve impulses and functions of vital organs are controlled by neurotransmitters. A neurotransmitter system includes cholinergic nervous system releasing acetylcholine and adrenergic nervous system releasing noradrenaline. Acetylcholine and noradrenaline are released by stimulation in central and peripheral nervous systems.

Additionally, in the central nervous system, there are many important neurotransmitters such as dopamine, serotonin and inhibitory GABA (γ-aminobutyric acid). Among them, serotonergic nervous system is closely related to mental illness such as anxiety, worry and melanocholia. It is known that the distribution of serotonin receptors is remarkably reduced in patients with schizophrenia or dementia. The serotonergic system in the brain is an important neurotransmitter system that controls actions including worry and emotional anxiety, and physical functions.

It is also known that the serotonergic system having various receptor subtypes is a very important neurotransmitter system in the brain and is involved in the regulation of various physiological functions and mental state.

Serotonin receptors activated by 5-HT have been divided into at least seven classes (5-$HT_{1-7}$), and each class has been further subdivided into different subtypes (A, B, . . . ). 5-$HT_{1A}$, which is one of the serotonin receptor subtypes, functions as a somatodendritic autoreceptor (presynaptic) in the dorsal raphe nucleus and as a postsynaptic receptor for 5-HT in terminal field areas.

Numerous research studies on agonists and antagonists for 5-$HT_{1A}$ receptors have been extensively conducted and excellent compounds were obtained. WAY100635, which is an arylpiperazine compound, is known as a typical antagonist. It was identified that WAY100635 is an important ligand for imaging 5-$HT_{1A}$ receptor.

The antagonists are important ligands for imaging 5-$HT_{1A}$ receptor. Radioactive ligands (radioligands) are obtained by labeling antagonists with radioactive isotopes such as carbon-11, fluorine-18 and iodine-125, etc.

A radioactive ligand of WAY100635 is synthesized by labeling carbon of methoxy or carbonyl group of WAY100635 with carbon-11. Central 5-$HT_{1A}$ receptors in the human brain are imaged by positron emission tomography (PET) using the radioligand.

The radioligand meets almost all requirements. However, it has a disadvantage that it is metabolized by amide hydrolysis in the human liver. It has another disadvantage that isotopes such as carbon-11 (halflife=20 min.) and fluorine-18 (halflife=2 hrs) have to be synthesized at cyclotron, and their halflives are too short, thereby resulting in limitation in the application thereof.

It has further disadvantages that iodine-125 has to be prepared one by one and it has to be applied only for animals because its halflife is too long.

Therefore, the development of new compounds that have a high affinity for 5-$HT_{1A}$ without problem of amide hydrolysis and is labeled with technetium (Tc) having radiochemically optimum conditions (easy manufacturability, halflife, radioactive level, easy purchase), without labeling of arylpiperazine compounds with carbon-11 or fluorine-18, is required.

In the other hand, a method of synthesizing WAY100635 derivatives by a conventional heat treatment had many problems that a large amount of solvent is required, reaction time is long and yield is low.

As a method to solve these problems, green chemistry began to draw attention recently and organic synthesis, which can reduce by-products, waste production and energy cost, is highlighted. An example of the organic synthesis is microwave irradiation (MWI) that induces direct coupling between reaction molecules and shows thermal conductivity leading to rapid rise in reaction temperature. MWI has outstanding advantages of shorter reaction time, higher yield, easier work-up and cleaner reaction due to less side reactions than organic synthesis according to a conventional heating.

The inventors have conducted numerous studies in order to solve the problems of the amide hydrolysis and of the conventional organic synthesis using heating. As a result, new arylpiperazine derivatives are synthesized by acylation of 2-aminopyridine and reduction of the arylpiperazine using microwave irradiation instead of the conventional heating method, and thiol compounds are synthesized by coupling the derivatives with $N_2S_2$ radioligand.

It was identified that the compounds have a high affinity for 5-$HT_{1A}$ and can be labeled with technetium that is the most useful radioactive isotope for nuclear-medicine imaging diagnosis. Based on these findings, the present invention has been completed.

SUMMARY OF THE INVENTION

An object of the present invention is to provide new, chelating ligand-coupled, Tc-labeled arylpiperazine derivatives that have no problem of amide hydrolysis in metabolism, have a high affinity for serotonin receptor, and can be labeled with technetium, which is an optimum radionuclide, thus being usefully applied for monitoring neurodegenerative diseases or neurological diseases, and to provide a method for the synthesis thereof and pharmaceutical kits including the same.

In order to achieve the object, the present invention provides new arylpiperazine derivatives coupled with chelating ligand for imaging serotonin receptor, represented by the following chemical formula (1):

[Chemical Formula 1]

Additionally, in order to achieve the object, the present invention provides a method for the synthesis of arylpiperazine derivatives coupled with MAMA-disulfide derivative ligand, or N₂S₂ or dimethyl-N₂S₂ ligand comprising the steps of:

(a) synthesizing arylpiperazine derivatives under microwave irradiation;

(b) synthesizing MAMA-disulfide derivative ligand, N₂S₂ or dimethyl-N₂S₂ ligand; and (c) synthesizing the compound (1) by coupling the arylpiperazine derivatives with the ligands under microwave irradiation.

Additionally, in order to achieve the object, the present invention provides a method for the synthesis of arylpiperazine derivatives of a chemical formula (1) by labeling arylpiperazine derivatives of the chemical formula (1) coupled with MAMA-disulfide derivative ligand, N₂S₂ or dimethyl-N₂S₂ ligand with technetium, under microwave irradiation, in the presence of pertechnetate ion, using tetrahydroborate exchange resin as a reducing agent.

In order to accomplish the object, the present invention further provides pharmaceutical kits including a sterilized vessel or a vial containing the compound of the chemical formula (1) with a reducing agent in lyophilized form, without a pyrogen.

DETAILED DESCRIPTION OF THE INVENTION

Hereinafter, the present invention will be described in detail.

A compound according to the present invention includes an arylpiperazine derivative coupled with MAMA-disulfide derivative ligand, N₂S₂ or dimethyl-N₂S₂ ligand that can selectively bind with serotonin receptor such as 5-HT$_{1A}$. The ligand is radiolabeled with radioactive technetium via the chelating ligand coupled to the arylpiperazine derivative. In the present invention, 'Ch' means a chelating ligand.

An arylpiperazine derivative coupled with MAMA-disulfide derivative ligand, N₂S₂ or dimethyl-N₂S₂ ligand according to the present invention, which is useful for imaging serotonin receptor, may be represented by the following a chemical formula (1):

[Chemical Formula 1]

wherein, X, Y, and Z are selected from the group consisting of (a), (b), (c), (d), and (e):
(a) X, Y, Z=H, C(OCH₃), CH;
(b) X, Y, Z=OCH₃, CH, CH;
(c) X, Y, Z=H, C(Cl), CH;
(d) X, Y, Z=H, N, CH;
(e) X, Y, Z=H, N, N; and
(f) Ch=chelating ligand.

Chelating ligand useful for the present invention includes all tridentate or tetradentate ligands which form neutral complexes by coupling with technetium. The chelating ligand is coupled with serotonin receptor linker by covalent bond. Preferable chelating ligand includes a plurality of N or S atoms to bind with radionuclide by coordinate bond.

Preferable examples of ligands according to the present invention are MAMA-disulfide compound and N₂S₂ or dimethyl-N₂S₂ compound represented by the following chemical formulas.

[Chemical Formula 2]

[Chemical Formula 3]

[Chemical Formula 4]

[Chemical Formula 5]

wherein, X' is selected from Cl, Br, or I; and

R may be selected from the group consisting of protecting groups represented by the following chemical formulas, and alkyl groups consisting of —CH$_3$, —C$_2$H$_5$, —C$_3$H$_7$ and —C$_4$H$_9$.

The chelating ligands may form the following complexes via coordinate bond with radionuclide such as technetium:

[Chemical Formula 6]

[Chemical Formula 7]

[Chemical Formula 8]

[Chemical Formula 9]

wherein R and X' groups are the same as defined in the above.

Preferable exemplary embodiments according to the present invention may use chelating ligands formed from monoaminomonoamino("MAMA") compounds having the structure of chemical formula 2 or 3, or from N$_2$S$_2$ and dimethyl-N$_2$S$_2$ compounds having the structure of chemical formula 4 or 5. The chelating ligand is usually attached to serotonin receptor via nitrogen, sulfur or R.

Preferable radiolabeled compounds according to the present invention have target selectivity to identify a desired target by passing through blood-brain barrier. In the case that the radiolabeled compounds have to pass through the blood-brain barrier, the chelating ligands usefully used in the present invention can form neutral complexes with radionuclides and have liposolubility.

Therefore, the radiolabeled compounds according to the present invention can be usefully applied as an agent for imaging neurological diseases.

A compound for imaging serotonin receptor according to the present invention represented by the chemical formula (1) is prepared by the steps of:

(a) synthesizing arylpiperazine derivatives under microwave irradiation;

(b) preparing chelating ligands separately under microwave irradiation; and (c) coupling the arylpiperazine derivatives and the chelating ligands under microwave irradiation.

In the step (a), the arylpiperazine derivatives may be prepared by conventional methods. However, they may preferably be prepared using microwave irradiation method that is easier, simpler and can synthesize products in shorter reaction time and in higher yield than the conventional methods.

Figure 1:
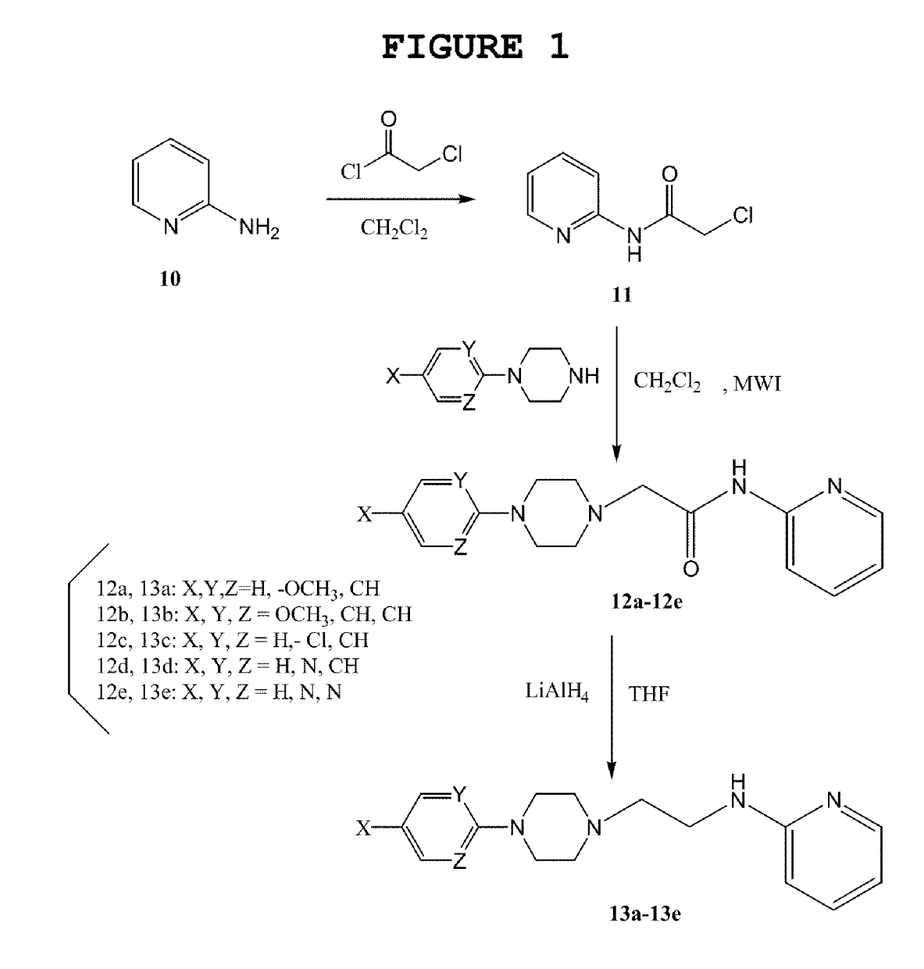
FIG. 1 is a reaction scheme for the preparation of an arylpiperazine derivative according to an embodiment of the present invention.

The reaction for the synthesis of arylpiperazine derivatives was schematically shown in FIG. 1.

2-aminopyridine (chemical formula 10) is used as a starting material and treated with chloroacetyl chloride in a solvent of dichloromethane to prepare a compound (11). The compound (11) is reacted with arylalkylpiperazine in the presence of a base of potassium carbonate to prepare a compound (12). The compound (12) is reduced by a reducing agent of lithium aluminum hydride to provide a desired compound (13) of arylpiperazine derivative.

In this case, each reaction step may preferably be performed under microwave irradiation. Microwave irradiation method has outstanding advantages of cleaner reactions due to less side reactions, easier work-up, simpler reaction, shorter reaction time, and higher yield than a conventional heating synthesis.

In the step (b), as described above, MAMA-disulfide ligand, or N$_2$S$_2$ or dimethyl-N$_2$S$_2$ ligand, which is used as a chelating ligand, is prepared.

Figure 2:
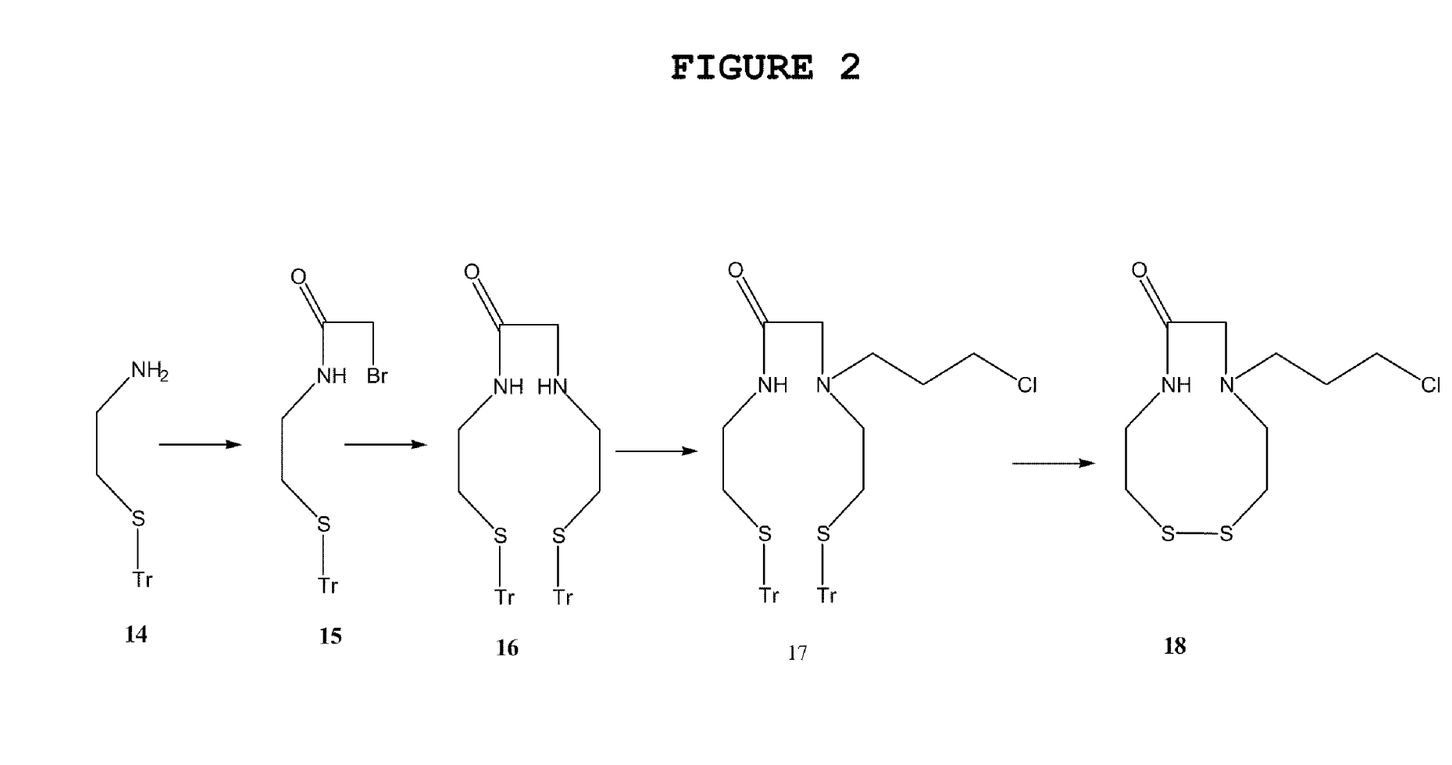
FIG. 2 is a scheme for the preparation of a chelating ligand according to an embodiment of the present invention.
Figure 3:
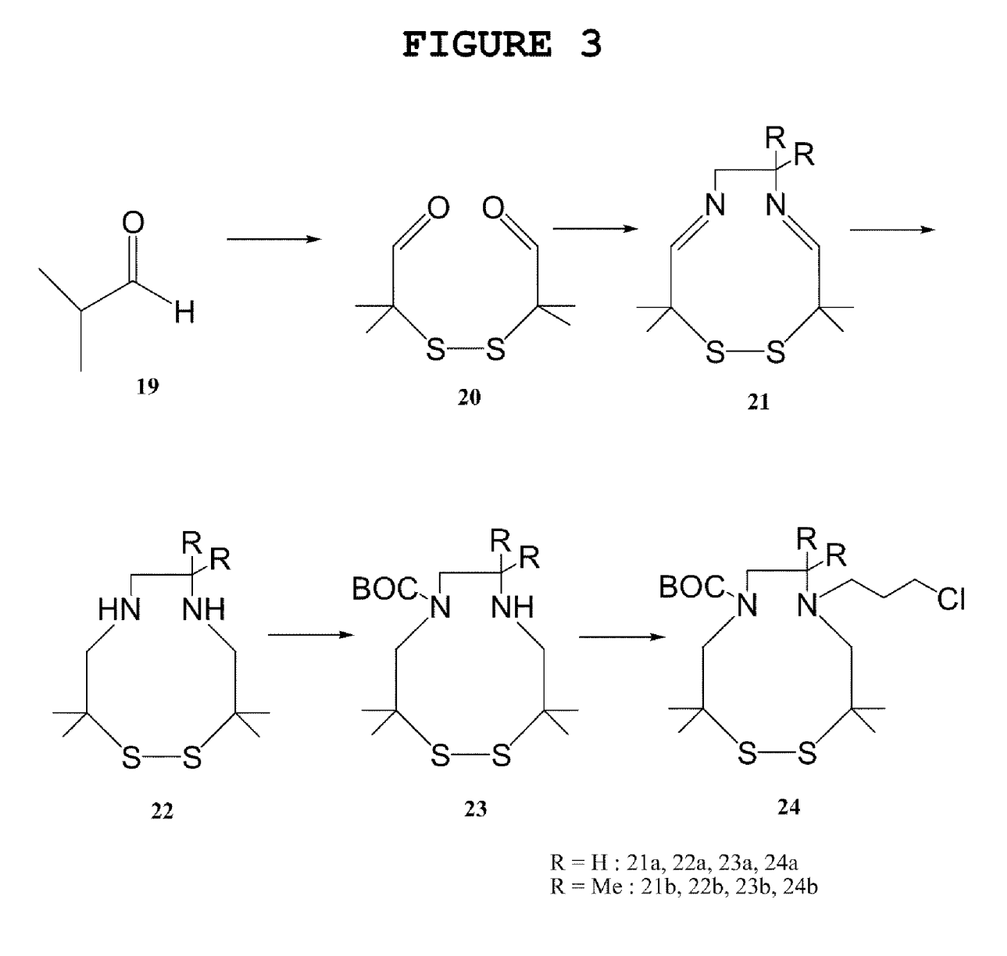
FIG. 3 is a scheme for the preparation of a chelating ligand according to another embodiment of the present invention.

Examples of the reactions for the synthesis of MAMA-disulfide ligand and N$_2$S$_2$ or dimethyl-N$_2$S$_2$ ligand are schematically shown in FIG. 2 and FIG. 3.

In the step (c), the compound (13) prepared in the step (a) and the chelating ligands prepared in the step (b) are coupled under microwave irradiation to provide a desired compound (1) of arylpiperazine derivatives coupled with MAMA-disulfide ligand, N$_2$S$_2$ or dimethyl-N$_2$S$_2$ ligand.

The desired compound (1) may preferably be prepared in short reaction time and in high yield by using potassium carbonate as a solvent and microwave irradiation. The reaction for the synthesis of the compound (1) was schematically shown in FIG. 4.

Arylpiperazine derivatives coupled with MAMA-disulfide ligand, N$_2$S$_2$ or dimethyl-N$_2$S$_2$ ligand, which are synthesized as described above, may be treated so as to include metal atoms (M), preferably a radionuclide such as $^{99}$Tc, $^{99m}$Tc, $^{188}$Re, or $^{186}$Re, more preferably a radionuclide such as $^{99m}$Tc, and thereby forming M-labeled complexes.

The radionuclide complexes of technetium or rhenium may be prepared by reacting the compound (1) with pertechnetate ion or perrhenate ion in the presence of a suitable reducing agent by conventional methods. The radionuclide complexes are preferably prepared in high yield by heating for a time enough to complete the reaction, preferably 5 to 10 min., under microwave irradiation.

The compound may be dissolved in a proper solvent with a reducing agent and then pertechnetate was added thereto.

Tetrahydroborate exchange resin may be used as a reducing agent suitable for the present invention.

The present invention further provides pharmaceutical kits, preferably the kits including a sterilized vessel or a vial containing the compound (1) with a reducing agent, preferably tetrahydroborate exchange resin, in lyophilized form, without a pyrogen.

The composition lyophilized in this form can be directly reconstituted with water, saline or buffer solution, preferably in the range of pH 5 to 8, more preferably in the case of adding the buffer solution having physiological pH.

In the case that a radionuclide metal is technetium, the pertechnetate ion solution obtained from a technetium generator may be used for the reconstitution.

Generally, a radiopharmaceutical kit includes a sealed and sterilized non-pyrogenic unit-dose (or multiple-dose) vial containing the purified compound (1) and a reducing agent for technetium, preferably in lyophilized form.

Each vial may contain the compound (1) and the reducing agent in amounts enough for producing technetium necessary for imaging, generally about 5 to 30 mCi according to the weight of a mammal to be imaged.

When used, technetium, preferably [$^{99m}$Tc] pertechnetate ion in saline is sterilely injected to each vial and the mixture is reacted for enough time for forming a labeled complex. After the reaction, the prepared radiopharmaceuticals can be immediately used.

A radiopharmaceutical composition according to the present invention has effective-dose radiation for a specific mammal and may be prepared in pharmaceutical carriers suitable for imaging a target object, for example common saline.

The radiopharmaceutical composition may be intravenously injected into the mammal. After injection, the target site of the mammal, for example the brain, may be scanned under gamma camera or other equipment suitable for radioactive diagnostic imaging.

For good quality images, labeling yield of technetium coupled in the radiopharmaceuticals may preferably be 70% or more after the reconstitution of the lyophilized mixture and labeling. Low yield leads to low quality images and additional purification may undesirably be needed in order to overcome this problem.

Radiopharmaceutical products for imaging brain receptors contain radioactive isotope-labeled compounds having a high binding affinity to various receptors and are helpful in obtaining various information.

The development of radioligands selectively binding to specific nerve receptors allows body-imaging of nerve receptors such as dopamine, serotonin, acetylcholine, benzodiazepine and the like, and monoamine transporter or reuptake site.

The present invention will be described in more detail with reference to the following exemplary embodiments. However, these examples are provided for the purpose of illustration only and should not be construed as limiting the scope of the invention, which will be apparent to one skilled in the art.

EXAMPLE 1

Synthesis of Arylpiperazine Derivative

Synthetic procedure for the preparation of arylpiperazine derivative was schematically shown in FIG. 1.

1) Synthesis of 2-(chloroacetyl)amidopyridine (11)

2-aminopyridine (2.8 g, 30 mmol) was dissolved in dichloroethane (25 ml) in a 50 ml-glass vessel and chloroacetyl chloride was added dropwise thereto.

The glass vessel was capped with a TFM Teflon cover and placed in a rotor in a microwave reactor. The mixture was irradiated by microwave at 300 W and 80° C., for 5 min. After irradiating for 5 min., the reaction mixture was adjusted to pH9 with a saturated aqueous solution of sodium hydroxide and extracted twice with dichloroethane.

The organic layer was dried over anhydrous sodium sulfate. The solvent was removed by using a rotary evaporator and the desired pink solid product of 4.9 g (97%) was obtained by recrystallization with acetonitrile.

mp 110-115° C.;

IR (KBr) 3443, 3226, 1683, 1581, 1330, 1198, 775 cm$^{-1}$;

$^1$H NMR (CDCl$_3$) 4.2 (2H, s), 7.1 (1H, d), 7.7 (1H, t), 8.2 (1H, d, J=8.3 Hz), 8.4 (1H, d, J=4.9 Hz), 8.95 (1H, bs);

$^{13}$C NMR (CDCl$_3$) 43.2, 111.4, 121.0, 139.1, 148.2, 150.7, 164.9;

EIMS m/z 170.6 (M$^+$)

2) Synthesis of 2-(1-(4-arylpiperazinyl))-N-(2-pyridyl)acetamide (12a-12e)

A solution of arylpiperazine (5.9 mmol) and 2-(chloroacetyl)amidopyridine (1.0 g, 6 mmol) dissolved in acetonitrile (30 ml) was added into a 50 ml-glass vessel containing K$_2$CO$_3$ (1.6 g, 12 mmol).

The reaction vessel was capped with a TFM Teflon cover and placed in a rotor in a microwave reactor. The mixture was irradiated at 300 W for 5 min. (12a, 12b) or 20 min (12c-12e) at 80° C. After irradiating for 5-20 min., the resulting mixture was cooled to room temperature.

The resulting mixture was dissolved in water and extracted twice with dichloromethane. The organic layer was washed successively with water and brine and dried over anhydrous sodium sulfate. A crude product was obtained by evaporation of solvent and purified by column chromatography.

2-a) Synthesis of 2-(1-(4-(2-methoxyphenyl)piperazinyl))-N-(2-pyridyl) acetamide (12a)

Except that irradiation time of microwave is 5 min., the same synthesis procedure as described above was carried out by using 1.0 ml of 1-(2-methoxyphenyl)piperazine.

A desired product as a white solid was obtained by using hexane/ethylacetate (8/2) as an elution.

Yield: 1.5 g (81%)

mp 84° C.;

IR (KBr) 3333, 3302, 1696, 1593, 1301, 1181 cm$^{-1}$;

$^1$H NMR (CDCl$_3$) 2.8 (4H, m), 3.2 (4H, m), 3.8 (3H, s), 6.8-7.1 (5H, m), 7.7 (1H, m), 8.95 (1H, bs);

$^{13}$C NMR (CDCl$_3$) 51.5 54.1 56.1, 65.3, 115.0, 119.0, 120.5, 138.5, 145.2, 148.3, 151.0, 154.5;

EIMS m/z 327 (M+1)$^+$, 326 (M$^+$).

2-b) Synthesis of 2-(1-(4-(4-methoxyphenyl)piperazinyl))-N-(2-pyridyl) acetamide (12b)

Except that irradiation time of microwave is 5 min., the same synthesis procedure as described above was carried out by using 1.5 g of 1-(4-methoxyphenyl)piperazine and dihydrochloride.

A desired product as a white solid was obtained by using hexane/ethylacetate (8/2) as an elution.

Yield: 1.4 g (75%)

mp 125-130° C.;

IR (KBr) 3448, 3301, 1688, 1574, 1299, 1181 cm$^{-1}$;

$^1$H NMR (CDCl$_3$) 2.8 (4H, m), 3.1 (4H, m), 3.2 (2H, s), 3.7 (3H, s), 6.7 (2H, m), 6.8 (2H, m), 6.9 (1H, t), 7.7 (1H, m), 8.2 (1H, dd, J=5.9 Hz, J=8.3 Hz), 9.5 (1H, bs);

$^{13}$C NMR (CDCl$_3$) 51.3, 54.0, 56.0, 65.5, 114.7, 114.9, 119.0, 120.3, 138.7, 145.6, 148.4, 151.4, 154.7,

EIMS m/z 326 (M$^+$).

2-c) Synthesis of 2-(1-(4-(2-chlorophenyl)piperazinyl))-N-(2-pyridyl) acetamide (12c)

Except that irradiation time of microwave is 20 min., the same synthesis procedure as described above was carried out by using 1.4 g of 1-(2-chlorophenyl)piperazine and monohydrochloride.

A desired product as a yellow solid was obtained by using hexane/ethylacetate (7/3) as an elution.

Yield: 1.7 g (87%)

mp 104-107° C.;

IR (KBr) 3447, 3316, 1694, 1588, 1282, 1200 cm$^{-1}$;

$^1$H NMR (CDCl$_3$) 1.9 (4H, m), 3.2 (4H, m), 3.2 (2H, s), 6.9-7.1 (3H, m), 7.2 (1H, d, J=7.5 Hz), 7.4 (1H, d, J=7.8 Hz), 7.7 (1H, m), 8.3 (2H, dd, J=5.7 Hz, J=16.2 Hz), 9.6 (1H, bs);

$^{13}$C NMR (CDCl$_3$) 51.1, 54.0, 62.4, 114.5, 120.4, 121.0, 124.6, 128.1, 129.3, 131.1, 138.9, 148.2, 151.3;

EIMS m/z 331.1 (M+1)$^+$, 330 (M$^+$)

2-d) Synthesis of 2-(1-(4-pyridylpiperazinyl))-N-(2-pyridyl)acetamide (12d)

Except that irradiation time of microwave is 20 min., the same synthesis procedure as described above was carried out by using 0.9 ml of 1-(2-pyridyl)piperazine.

A desired product as a yellow solid was obtained by using hexane/ethylacetate (5/5) as an elution.

Yield: 1.2 g (72%)

mp 125° C.;

IR (KBr) 3435, 3311, 1700, 1297, 1184 cm$^{-1}$;

$^1$H NMR (CDCl$_3$) 2.7 (4H, m), 3.2 (2H, s), 3.6 (4H, m), 6.5 (1H, d), 6.6 (2H, m), 7.5 (1H, m), 7.7 (1H, m), 8.1-8.3 (2H, m), 9.6 (1H, bs);

$^{13}$C NMR (CDCl$_3$);

EIMS m/z 299 (M+2)$^+$, 298 (M+1)$^+$.

2-e) Synthesis of 2-(1-(4-pyrimidylpiperazinyl))-N-(2-pyridyl)acetamide (12e)

Except that irradiation time of microwave is 20 min., the same synthesis procedure as described above was carried out by using 0.4 g of 1-(2-pyrimidyl)piperazine and dihydrochloride.

A desired product as a brown solid was obtained by using hexane/ethylacetate (7/3) as an elution.

Yield: 1.1 g (65%)

mp 126-128° C.;

IR (KBr) 3436, 3303, 1698, 1297, 1189 cm$^{-1}$;

$^1$H NMR (CDCl$_3$) 2.8 (4H, m), 3.2 (4H, m), 3.3 (2H, s), 3.8 (3H, s), 6.5-7.1 (3H, m), 7.6-7.9 (2H, m), 8.3 (2H, m), 9.6 (1H, bs);

$^{13}$C NMR (CDCl$_3$) 43.7, 44.2, 110.9, 114.3, 118.8, 139.6, 146.2, 152.8, 154.2, 158.2, 161.9;

EIMS m/z 299 (M+1)$^+$, 298 (M$^+$).

3) Synthesis of 1-(aryl)-4-(2-(2-pyridylamino)ethyl) piperazine (13a-13e)

Lithium aluminum hydride (11.0 mmol, 4 equiv.) was dissolved in anhydrous tetrahydrofuran (7.5 ml) and then directly added dropwise into a 50 ml-glass vessel containing the solution of 2-(1-(4-arylpiperazinyl))-N-(2-pyridyl)acetamide (2.75 mmol) dissolved in anhydrous tetrahydrofuran (15 ml).

The reaction vessel was capped with a TFM Teflon cover and placed in a rotor in a microwave reactor. The mixture was irradiated at 300 W and 80° C., for 5 min. After irradiating for 5 min., the reaction mixture was cooled to room temperature.

The resulting mixture was quenched with a saturated ammonium chloride solution at 0° C. and extracted twice with dichloromethane. The organic layer was washed successively with water and brine, dried over anhydrous sodium sulfate, filtered and concentrated by using a rotary evaporator.

The residue was purified by column chromatography.

3-a) Synthesis of 1-(2-methoxyphenyl)-4-(2-(2-pyridylamino)ethyl)piperazine (13a)

The same synthesis procedure as described above was carried out by using 0.9 g of 2-(1-(4-(2-methoxyphenyl)piperazinyl))-N-(2-pyridyl) acetamide.

A desired product as a needle form was obtained by using hexane/ethylacetate (8/2) as an elution.

Yield: 1.6 g (92%)

mp 63-64° C.;

IR (KBr) 3407, 3269, 2955, 1359, 1309, 1150 cm$^{-1}$;

$^1$H NMR (CDCl$_3$) 2.8 (6H, m), 3.1 (4H, m), 3.4 (2H, s), 3.8 (3H, s), 6.4 (1H, d), 6.5 (1H, t), 6.9-7.1 (4H, m), 7.4 (1H, t), 8.1 (1H, d);

$^{13}$C NMR (CDCl$_3$) 38.7, 50.7, 53.6, 55.8, 57.3, 107.8, 111.7, 113.1, 118.7, 121.4, 123.5, 137.7, 141.5, 148.3, 152.7, 159.1;

EIMS m/z 313 (M+1)$^+$.

3-b) Synthesis of 1-(4-methoxyphenyl)-4-(2-(2-pyridylamino)ethyl) piperazine (13b)

The same synthesis procedure as described above was carried out by using 0.9 g of 2-(1-(4-(4-methoxyphenyl)piperazinyl))-N-(2-pyridyl) acetamide.

A desired product as a yellow solid was obtained by using hexane/ethylacetate (7/3) as an elution.

Yield: 1.3 g (80%)

mp 82-85° C.;

IR (KBr) 3405, 3248, 2948, 1358, 1270, 1186 cm$^{-1}$;

$^1$H NMR (CDCl$_3$) 2.9 (6H, m), 3.2 (4H, m), 3.6 (2H, s), 3.8 (3H, s), 5.7 (1H, bs), 6.5 (2H, m), 6.9 (4H, m), 7.4 (1H, m), 8.1 (1H, d, J=3.8 Hz);

$^{13}$C NMR (CDCl$_3$) 38.3, 50.2, 53.7, 55.5, 57.1, 107.5, 112.1, 113.3, 118.5, 121.1, 123.1, 137.2, 141.1, 148.5, 152.7, 158.8;

EIMS m/z 313 (M+1)$^+$.

3-c) Synthesis of 1-(2-chlorophenyl)-4-(2-(2-pyridylamino)ethyl) piperazine (13c)

The same synthesis procedure as described above was carried out by using 0.9 g of 2-(1-(4-(2-chlorophenyl)piperazinyl))-N-(2-pyridyl) acetamide.

A desired product as an oily form was obtained by using hexane/ethylacetate (5/5) as an elution.

Yield: 1.3 g (78%)

IR (neat) 3447, 3316, 2942, 1375, 1303, 1286, 1201 cm$^{-1}$;

$^1$H NMR (CDCl$_3$) 2.9 (6H, m), 3.2 (4H, m), 3.3 (2H, m), 5.1 (1H, bs), 6.3 (1H, d, J=8.4 Hz), 6.5 (1H, m), 6.9 (3H, m), 7.2-7.3 (2H, m), 8.0 (1H, d, J=3.9 Hz);

$^{13}$C NMR (CDCl$_3$) 38.9, 51.7, 53.4, 57.1, 107.4, 113.1, 120.8, 124.1, 128.0, 129.2, 131.0, 137.7, 148.6, 149.7, 159.2;

EIMS m/z 317 (M$^+$).

3-d) Synthesis of 1-(2-pyridyl)-4-(2-(2-pyridylamino)ethyl)piperazine (13d)

The same synthesis procedure as described above was carried out by using 0.8 g of 2-(1-(4-pyridylpiperazinyl))-N-(2-pyridyl)acetamide.

A desired product as an oily form was obtained by using hexane/ethylacetate (6/4) as an elution.

Yield: 1.0 g (65%)

IR (neat) 3373, 2995, 2924, 1379, 1309, 1125 cm$^{-1}$;

$^1$H NMR (CDCl$_3$) 2.6 (6H, m), 3.3 (2H, m), 3.5 (4H, m), 5.1 (1H, bs), 6.3-6.6 (4H, m), 7.4 (2H, m), 8.0 (1H, t), 8.1 (1H, d, J=4.1 Hz);

$^{13}$C NMR (CDCl$_3$) 38.9, 51.7, 53.4, 57.1, 107.4, 113.1, 120.8, 124.1, 128.0, 129.2, 131.0, 137.7, 148.6, 149.7, 159.2;

EIMS m/z 284 (M+1)$^+$.

3-e) Synthesis of 1-(2-pyrimidyl)-4-(2-(2-pyridylamino)ethyl)piperazine (13e)

The same synthesis procedure as described above was carried out by using 0.8 g of 2-(1-(4-pyrimidylpiperazinyl))-N-(2-pyridyl)acetamide.

A desired product as an oily form was obtained by using hexane/ethylacetate (7/3) as an elution.

Yield: 0.9 g (63%)

IR (neat) 3436, 3303, 2927, 1360, 1305, 1154 cm$^{-1}$;

$^1$H NMR (CDCl$_3$) 2.8 (6H, m), 3.1 (4H, m), 3.4 (2H, s), 3.8 (3H, s), 6.4 (1H, d), 6.5 (1H, t), 6.8-7.1 (4H, m), 7.4 (1H, t), 8.1 (1H, d);

$^{13}$C NMR (CDCl$_3$) 38.8, 53.2, 57.4, 60.8, 107.9, 110.4, 113.2, 137.9, 148.0, 158.1, 158.9, 168.1;

EIMS m/z 285 (M+1)$^+$.

EXAMPLE 2

Synthesis of Chelating Ligand

1) Synthesis of 3-chloropropyl-MAMA-disulfide

A scheme for the preparation of 3-chloropropyl-MAMA-disulfide was schematically shown in FIG. 2.

1-a) Synthesis of S-triphenylmethyl-cysteamine (14)

Cysteamine hydrochloride (5 g, 43 mmol) was dissolved in trifluoroacetic acid (50 ml) at room temperature. Triphenylmethanol (11.5 g, 43 mol) was added in portions to the reaction mixture and the reaction mixture was subsequently stirred at room temperature for 1 hr.

The reaction mixture was evaporated under reduced pressure and dark orange oil was obtained.

After addition of hexane (3×100 ml), evaporation was repeated three times to remove traces of trifluoroacetic acid.

The residual oil was dispersed in a mixture of water (100 ml) and ethyl acetate (100 ml), and the mixture was neutralized with 10% NaHCO$_3$ solution.

The organic phase was separated, dried over anhydrous magnesium sulfate, and concentrated under reduced pressure.

The crude product was recrystallized with EtOH, filtered and a white solid was obtained.

Yield: 11.8 g (37 mol, 86%)

mp 174-175° C.;

IR (cm$^{-1}$, KBr pellet) 3442, 3020, 1683, 1592, 1493, 1442, 1430, 1192, 1131;

$^1$H NMR (CDCl$_3$) δ 7.44-7.46 (m, 6H, ArH), 7.21-7.36(m, 9H, ArH), 2.67(t, J=6.6 Hz, 2H, NCH$_2$), 2.29(t, J=6.6 Hz, 2H, SCH$_2$)

$^{13}$C NMR (CDCl$_3$) δ 144.3, 129.7, 128.6, 127.5, 67.8, 38.7, 29.3;

m/z 320.0 [M$^+$].

1-b) Synthesis of N-(2-bromoacetyl)-S-triphenylmethyl-cysteamine (15)

To a stirred, −20° C. solution of bromoacetyl bromide dissolved in dry dichloromethane, a solution of S-triphenylmethyl-cysteamine (14) (6 g, 19.2 mmol) and triethylamine dissolved in dry dichloromethane was added dropwise over 15 min.

The mixture was heated to room temperature, stirred for 15 min., and then quenched with water (30 ml). The layers were separated, and the organic layer was washed with 1 N HCl, water, 10% NaHCO$_3$ and saturated NaCl (30 ml, each).

The organic layer was dried over MgSO$_4$, filtered, and concentrated to the volume of 10 ml. The resulting product was triturated with hexane (30 ml), stored at room temperature and white crystals (3.9 g, 45%) were obtained.

After storing overnight in a freezer, a second crop of crystals (2.2 g, 26%) was obtained.

mp 133-134° C.;

IR (cm$^{-1}$, KBr pellet) 3223, 3078, 2924, 1654, 1577, 1586, 1486, 1438;

$^1$H NMR (CDCl$_3$) δ 7.46-7.42(m, 6H, ArH), 7.35-7.22(m, 9H, ArH), 3.83(s, 2H, CH$_2$Br), 3.13(q, J=6.3 Hz, 2H, SCH$_2$), 2.45 (t, J=6.3 Hz, 2H, SCH$_2$);

$^{13}$C NMR (CDCl$_3$) δ 165.5, 144.9, 129.9, 128.4, 127.3, 67.3, 39.1, 32.1, 29.5;

m/z 439.0 [M$^+$], 245.0, 243.0.

1-c) Synthesis of N-(2-tritylsulfanyl-ethyl)-2-(2-tritylsulfanyl-ethylamino) acetamide [MAMA-Tr$_2$] (16)

To a solution of bromide (15) (3 g, 6.8 mmol) and diisopropylamine (0.9 g, 6.8 mmol) dissolved in dichloromethane (40 ml), amine (14) (2.2 g, 6.8 mmol) was added as suspension of dichloromethane (20 ml).

The mixture was stirred at room temperature for 24 hrs, then quenched with water (60 ml) to separate the layers. The organic layer was washed with 10% NaHCO$_3$, water and saturated NaCl. The organic layer was dried over MgSO$_4$ and filtered.

White foam was obtained by purification with column chromatography.

Yield: 3.3 g (71%);

IR (cm$^{-1}$, KBr pellet) 3448, 1670, 1488, 1443;

¹H NMR (CDCl₃) δ 7.45-7.39(m, 12H, ArH), 7.31-7.18(m, 18H, ArH), 3.09(q, J=6.3 Hz, 4H, NCH₂), 3.05(s, 2H, SCH₂), 2.50-2.46(t, J=6.3 Hz, 2H, NCH₂), 2.41-2.34(q, J=6.6 Hz, 4H, OCNCH₂);

¹³C NMR (CDCl₃) δ 171.6, 145.1, 130.0, 128.3, 127.1, 67.1, 52.2, 48.7, 38.1, 32.7;

m/z 679.0 [M⁺].

1-d) Synthesis of 0.2-[(3-chloropropyl)-(2-tritylsulfanyl-ethyl)-amino]-N-(2-tritylsulfanyl-ethyl)-acetamide; [2-(3-chloropropyl)-MAMA-Tr₂] (17)

To a solution of MAMA-Tr₂ (16) (3 g, 4.4 mmol) and K₂CO₃ dissolved in DMF, 1-bromo-3-chloropropane (0.75 g, 4.8 mmol) was added.

The mixture was stirred at room temperature for 24 hrs, and after removal of DMF, dispersed in a mixture of water (30 ml) and dichloromethane (30 ml) to separate the layers. The organic layer was washed with 10% NaHCO₃, water and saturated NaCl.

The organic layer was dried over MgSO₄ and filtered.

White foam was obtained by purification with column chromatography.

Yield: 1.8 g (61%)

¹H NMR (CDCl₃) δ 7.45-7.42(m, 12H, ArH), 7.30-7.19(m, 18H, ArH), 3.470(t, J=6.3 Hz, 2H, CH₂Cl), 3.04(q, 4H, J=6.3 Hz, NCH₂), 2.97(s, 2H, COCH₂), 2.38(m, 2H, OCNCH₂);

¹³C NMR (CDCl₃) δ 170.8, 129.7, 128.1, 126.8, 66.8, 58.3, 54.0, 53.0, 51.9, 42.8, 38.1, 32.0, 30.0, 18.5;

m/z 755.2 [M⁺].

1-e) Synthesis of 8-(3-chloropropyl)-[1,2,5,8]dithiadiazecan-6-one; [3-chloropropyl-MAMA-disulfide] (18)

A solution of 3-chloropropyl-MAMA-Tr₂ (17) (1.5 g, 2 mmol) and mercury acetate (1.3 g, 4 mmol) dissolved in MeOH/EtOAc (20 ml. 1:1 v/v) was prepared.

The mixture was stirred at room temperature for 24 hrs, dispersed in a mixture of water (20 ml) and dichloromethane (20 ml) after removal of solvent, and then the layers were separated.

The organic layer was washed with 10% NaHCO₃, water and saturated NaCl. The organic layer was dried over MgSO₄ and filtered.

White foam was obtained by purification with column chromatography.

Yield: 0.45 g (84%)

2) Synthesis of N₂S₂ and dimethyl-N₂S₂

Scheme for the preparation of N₂S₂ and dimethyl-N₂S₂ was shown in FIG. 3.

2-a) Synthesis of 3,3,10,10-tetramethyl-3,6,7,10-tetrahydro-[1,2,5,8]dithiadiazecine (21a, 21b)

To a stirred, chilled (0° C.) solution of isobutylaldehyde (20 ml, 220 mmol) dissolved in carbon tetrachloride (35 ml), sulfur monochloride (8.8 ml, 11.01 mmol) was added dropwise.

The mixture was refluxed to 55-60° C. for over 6 hrs. The solvent was removed under reduced pressure, then the residue was washed with 1N NaOH and dissolved in ethylacetate (30 ml) washed with saturated NaCl solution.

The organic layer was dried over anhydrous Na₂SO₄ and evaporated under reduced pressure. The residue was dissolved in benzene (50 ml) and p-TsOH.

To this solution, ethylenediamine (7.3 ml, 110.1 mmol) was added dropwise while stirring. In the preparation of dimethylimine (21b), 1,2-diamino-2-methylethane was used instead of ethylenediamine.

After refluxing for 2 hrs, the residue was dissolved in chloroform (200 ml) and filtered with a sintered glass filter. The solvent was removed from the filtrate by rotary evaporation.

Then, the residue was recrystallized in acetonitrile or CH₃OH, washed with cold petroleum ether and a white solid was obtained.

Yield: 47.9 g (66%)

IR (cm⁻¹, KBr pellet) 3445, 2970, 2940, 2852, 2887, 1853, 1442, 1362, 1110;

¹H NMR (CDCl₃) δ 6.87(s, 2H, N=CH), 4.15(d, 2H, J=9.3 Hz, NCH₂), 3.25(d, J=9.3 Hz, N=CH), 1.46(s, 6H, CH₃), 1.38(s, 6H, CH₃);

¹³C NMR (CDCl₃) δ 168.0, 61.6, 53.2, 24.8, 21.7,;

m/z 230.0 [M⁺]

2-b) Synthesis of 3,3,10,10-tetramethyl-[1,2,5,8]dithiadiazecane (22a, 22b)

To a solution of imine (21, 21a) (5 g, 48 mmol) dissolved in methanol (100 ml), sodium cyanoborohydride (3 g, 48 mmol) was slowly added. Glacial acetic acid was added to adjust pH 5.

After stirring at room temperature for 2 hours, the solution was heated for 6 hours to reach 60° C. The reaction mixture was quenched with saturated NH₄Cl solution (30 ml) and the solvent was evaporated under reduced pressure.

The residue was dissolved in 1N NaOH (10 ml) and extracted with chloroform (50 ml×3).

The chloroform layer was washed with saturated NaCl solution, dried over anhydrous sodium sulfate in vacuum and an objective compound (8.1 g, 34.5 mmol) of yellowish oil was obtained.

IR (cm⁻¹, KBr pellet) 3448, 3243, 2948, 2924, 2881, 2798, 1470, 1361, 1266, 1245, 1149;

¹H NMR (CDCl₃) δ 2.95(d, 2H, J=12.3 Hz, NCHCMe), 2.76(s, 4H, NCH), 2.52(d, 2H, J=12.3 Hz, NCHCMe₂), 1.99 (b, 2H, NH), 1.32(s, 6H, CH₃), 1.20(s, 6H, CH₃);

¹³C NMR (CDCl₃) δ 58.7, 51.9, 46.6, 28.6, 26.3;

m/z 234.0 [M⁺].

2-c) Synthesis of N-BOC-3,3,10,10-tetramethyl-[1,2,5,8]dithiadiazecane (23a, 23b)

A stirred, chilled (0° C.) solution of diaminedisulfide (22, 22a) (5 g, 21 mmol) dissolved in dry dichloromethane (30 ml) was added dropwise to a solution of (BOC)₂O (4.6 g, 21 mmol) dissolved in dry dichloromethane (30 ml)

The mixture was heated to room temperature, stirred for 15 min., and then quenched with water (30 ml). The layers were separated, and the organic layer was washed with 10% NaHCO₃, water and saturated NaCl (30 ml, each)

The organic layer was dried over Na₂SO₄ and filtered. An objective compound (5.27 g, 75%) was obtained by purification with column chromatography.

$^1$H NMR (CDCl$_3$) δ 3.71(m, 2H, NCH$_2$), 3.52(d, 2H, J=15.5 Hz, NCH$_2$), 3.12 (d, 2H, J=13.2 Hz NCH$_2$), 2.8(d, 2H, J=13.2 Hz, NCH$_2$), 2.60(d, 2H, J=12.9 Hz NCH$_2$), 1.47(s, 9H, CH$_3$), 1.34-1.27(m, 12H, CH$_3$);

$^{13}$C NMR (CDCl$_3$) δ 157.2, 80.4, 53.0, 51.5, 50.4, 49.8, 31.8, 28.8, 25.3.

2-d) Synthesis of N-BOC-N'-(3-chloropropyl)-3,3,10,10-tetramethyl-[1,2,5,8]dithiadiazecane (24a, 24b)

To a solution of N-BOC-DADS (23, 23a) (3 g, 9 mmol) and K$_2$CO$_3$ dissolved in DMF (50 ml, 1-bromo-3-chloropropane (1.5 g, 9.9 mol) solution was added.

The mixture was stirred at room temperature for 24 hours, dispersed in a mixture of water (50 ml) and dichloromethane (50 ml) after removal of DMF, and then the layers were separated.

The organic layer was washed with 10% NaHCO$_3$, water and saturated NaCl. The organic layer was dried over MgSO$_4$ and filtered.

An objective compound (2.8 g, 66%) was obtained by purification with column chromatography.

EXAMPLE 3

Synthesis of 8-[3-({2-[4-(2-methoxy-phenyl)-piperazine-1-yl]-ethyl}-pyridin-2-yl-amino)-propyl]-[1,2,5,8]dithiadiazecan-6-one (1)

Figure 4:
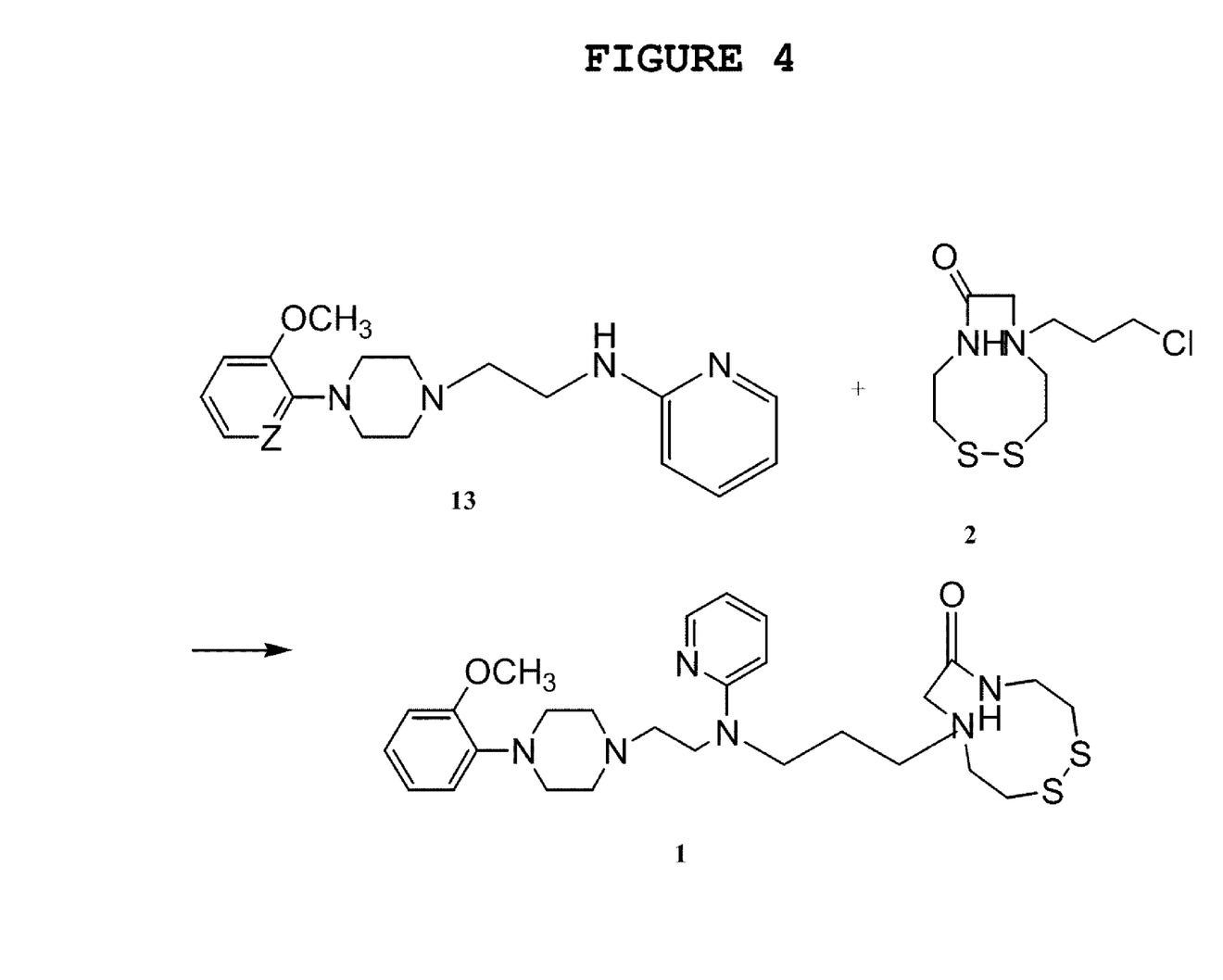
FIG. 4 is a scheme for the preparation of a chelating ligand-coupled arylpiperazine derivative according to another embodiment of the present invention.

Scheme for the preparation thereof was shown in FIG. 4.

A solution of 1-(2-methoxyphenyl)-4-(2-(2-pyridylamino) ethyl) piperazine (13) (0.62 g, 0.2 mmol) and 8-(3-chloropropyl)-[1,2,5,8]dithiadiazecan-6-one (2) (0.52 g, 0.2 mmol) dissolved in DMF was added into a 50 ml-glass vessel containing an excess of K$_2$CO$_3$.

The reaction vessel was capped with a TFM Teflon cover and placed in a rotor in a microwave reactor. The mixture was irradiated at 300 W and 130° C., for 30 min., and cooled to room temperature. The resulting mixture was successively evaporated, dissolved in water and extracted twice with dichloromethane.

The organic layer was washed successively with water and brine, and dried over anhydrous sodium sulfate. The solvent was evaporated and a crude product was obtained.

The crude product was purified by column chromatography, and a desired product as an oily form having yield of 0.07 g (20%) was obtained.

To obtain a derivative of WAY100635 that can be labeled efficiently with $^{99m}$Tc, a conjugate of WAY100635 derivative and MAMA-disulfide ([1,2,5,8]dithiadiazecan-6-one, a $^{99m}$Tc chelating agent) was synthesized.

Firstly, the possibility of coupling 1-(2-methoxyphenyl)-4-(2-(2-pyridylamino) ethyl) piperazine (13) with [1,2,5,8] dithiadiazecan-6-one via a chloropropyl spacer was investigated.

Compound 13 and [1,2,5,8]dithiadiazecan-6-one were successfully synthesized (in yields of 75% and 61%, respectively).

However, their coupling reaction was not successful by using conventional methods with minor modifications.

The coupling reaction of compound 13 and compound 2 was successfully achieved by a new method using microwave irradiation (yield 20%). TLC (Ethylacetate:n-Hexane: MeOH=:1:1:2, v/v):1, R$_f$=0.561, 2, R$_f$=0.929, 3, R$_f$=0.789; m/z 544.27[M+]557.1, 533.1.

EXAMPLE 4

Radiolabeling

Figure 5:
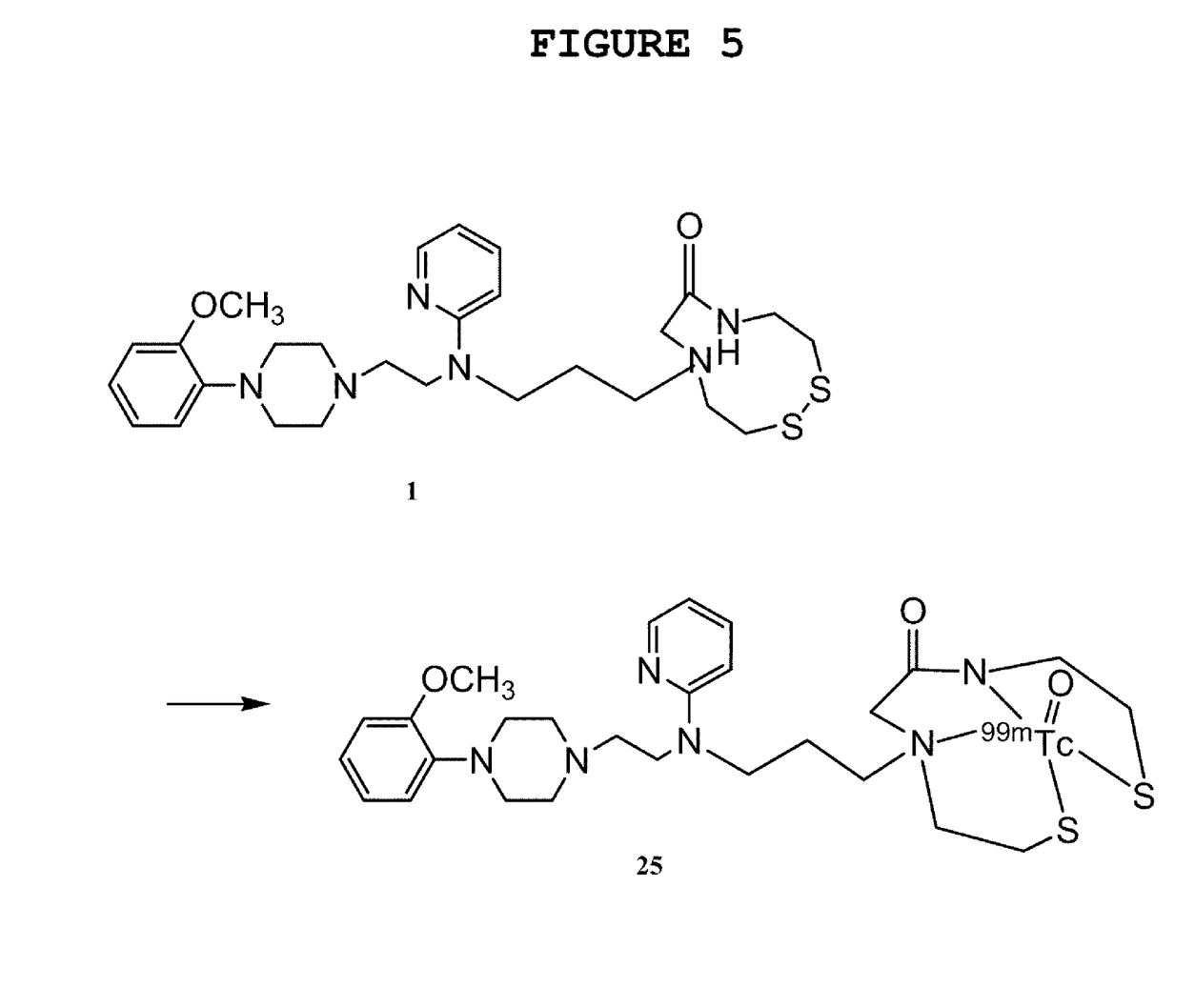
FIG. 5 is a scheme for the preparation of a $^{99m}$Tc-labeled, chelating ligand-coupled arylpiperazine derivative according to another embodiment of the present invention.

Radiolabeling reaction was schematically shown in FIG. 5. As shown in FIG. 5, $^{99m}$Tc-8-[3-({2-[4-(2-methoxy-phenyl)-piperazine-1-yl]-ethyl}1-pyridin-2-yl-amino)-propyl]-[1,2,5,8]dithiadiazecan-6-one (25) was synthesized by using Na$^{99m}$TcO$_4$, BER and DMSO, and reacting at room temperature for 30 min.

4-a) Tetrahydroborate Exchange Resin (BER)

A tetrahydroborate exchange resin (BER) was prepared by a conventional method.

Chloride-form resin (Amberlite™ ion exchange resin, 12.5 g) was slurry-packed with water into a 30 ml-fritted glass funnel mounted on a filter flask. Then, aqueous sodium borohydride solution (200 ml, 0.25 M) was slowly passed through the resin over a period of 30 min.

The resulting resin was washed thoroughly with distilled water and finally with ethanol (10 ml×3).

The borohydride-form anion exchange resin (BER) was then partially air-dried by removing ethanol on the surface thereof.

4-b) $^{99m}$Tc-Radiolabeling Using BER

To a vial containing 5 mg of BER, 0.1 ml of Na$^{99m}$TcO$_4$ (185 MBq) and a solution of compound (1) (0.07 g, 0.13 mmol) dissolved in DMSO were added at the same time.

The mixture was stirred at room temperature for 30 min under N$_2$ atmosphere, filtered with a membrane filter (0.22 μm), and then analyzed by RP-HPLC.

4-c) Results of Radiolabeling

Instant Thin-Layer Chromatography (ITLC)

ITLC-SG (silica gel) was performed using MEK and saline as a development solvent.

The results were shown in Table 1.

As shown in Table 1, the ITLC-SG of $^{99m}$Tc-complex (25) using MEK as a development solvent gave no peak at the solvent front where $^{99m}$TcO$_4$ would be expected.

Some $^{99m}$TcO$_2$ was observed at the origin, after $^{99m}$Tc-complex (25) was eluted with saline. These results indicate that $^{99m}$Tc-8-[3-({2-[4-(2-methoxy-phenyl)-piperazine-1-yl]-ethyl}-pyridin-2-yl-amino)-propyl]-[1,2,5,8]dithiadiazecan-6-one (25) having 99% of labeling efficiency was formed.

In the case of the conventional method using tin (II) chloride as a reducing agent, compound 25 was not observed.

TABLE 1

| Chromatographic system | | $^{99m}$Tc species at | |
|---|---|---|---|
| Support | Solvent | Origin | Solvent front |
| ITLC-SG | MEK | 100% of $^{99m}$Tc-complex (25) | 0% of $^{99m}$TcO$_4$$^-$ |
| ITLC-SG | Saline | 1% of $^{99m}$TcO$_2$ | 99% of $^{99m}$Tc-complex (25) |

Reversed Phase High Performance Liquid Chromatography (HPLC)

Radiochemical purity of $^{99m}$Tc-complex (25) was determined by HPLC using a C-18 reverse-phase column as a stationary phase and a water/ACN as a mobile phase, while maintaining a flow rate of 1 ml/min.

The retention times of $^{99m}$TcO$_4$—, $^{99m}$Tc-MAMA-disulfide moiety and $^{99m}$Tc-complex (25) are 3.0, 3.5 and 29.0 min, respectively.

The radiolabeling yield of compound 25 in the reaction mixture was found to be 95%. The complex is stable (>90%) for approximately 4 hours.

In the case of the conventional method using tin(II) chloride as a reducing agent, the formation of compound 25 was not observed.

Paper Electrophoresis

Filtered preparation was applied on a paper eluted with 0.1 M phosphate buffer (pH7.4) for 45 min. at a 400V (20V/cm).

Figure 6:
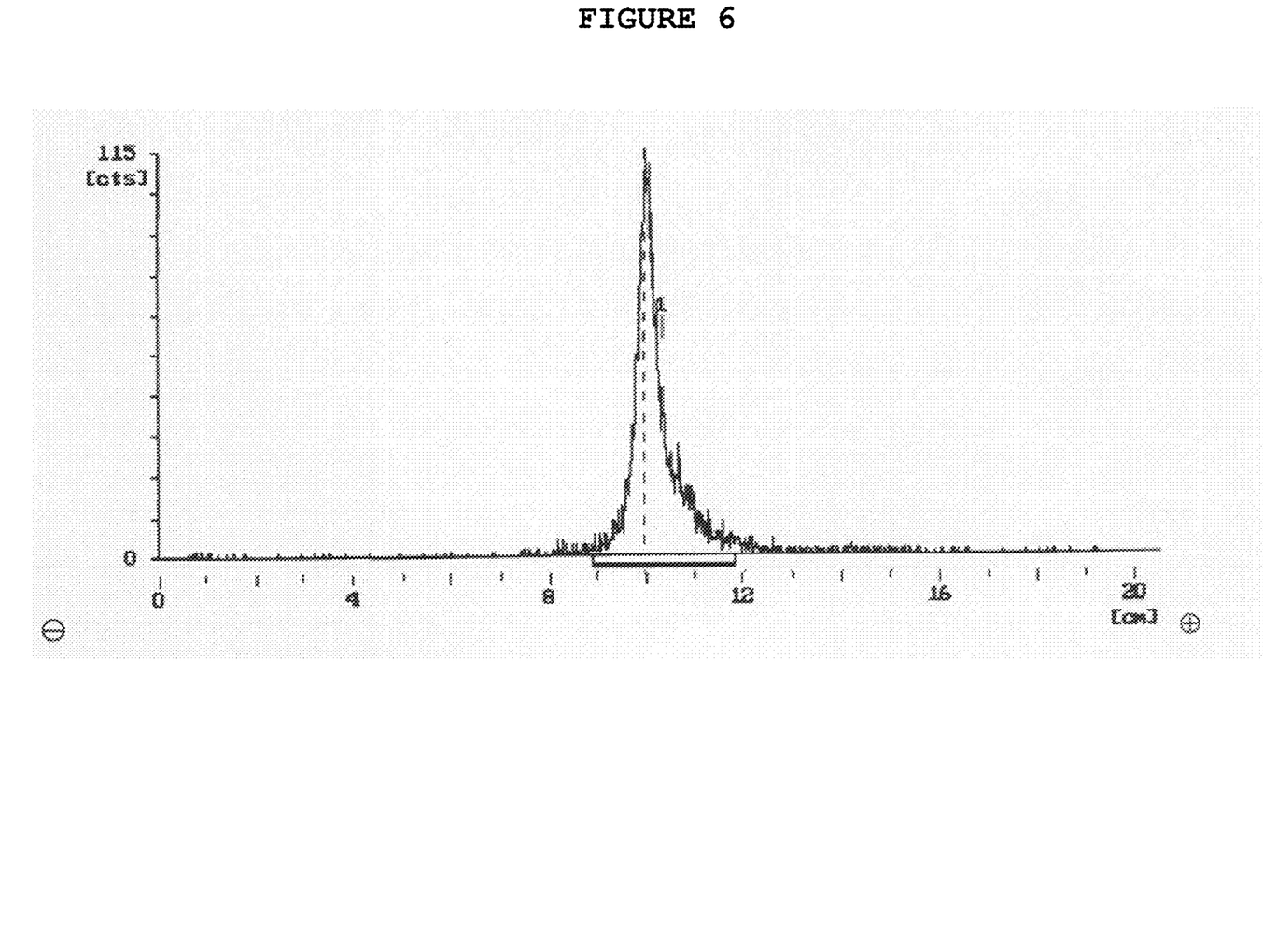
FIG. 6 is a paper electrophoresis chromatogram of a $^{99m}$Tc-complex according to an embodiment of the present invention.

The results were shown in FIG. 6. As shown in FIG. 6, neutral charge was observed in paper electrophoresis in aqueous solution.

Animal Study

Figure 7:
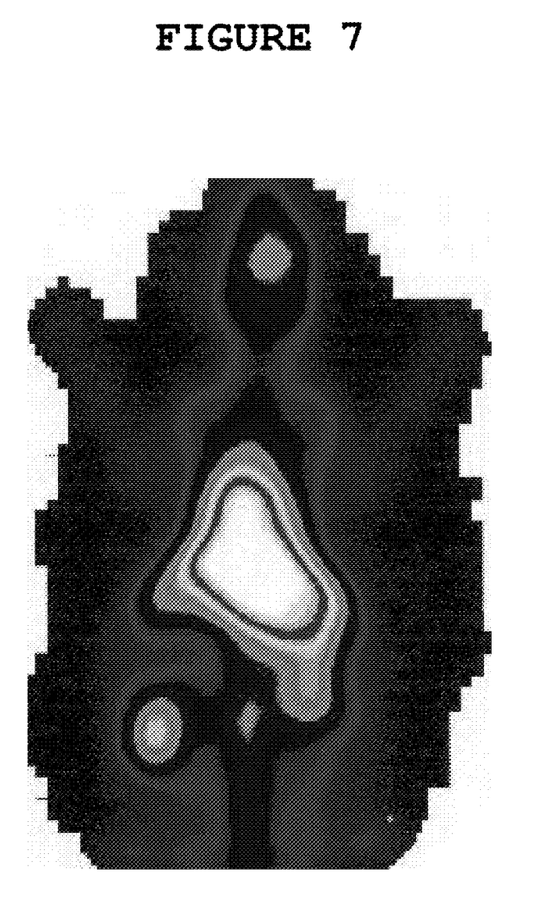
FIG. 7 is a photo showing an image scan of a rabbit after intravenous injection of a $^{99m}$Tc-complex according to an embodiment of the present invention.

Static image of male New Zealand white rabbits scanned at 5 and 10 min. After the intravenous injection of $^{99m}$Tc-complex (25) is shown in FIG. 7.

At an image of 5 min. after the injection, high activity was found in the liver. A trace amount of $^{99m}$Tc-8-[3-({2-[4-(2-methoxy-phenyl)-piperazin-1-yl]-ethyl}-pyridin-2-yl-amino)-propyl]-[1,2,5,8]dithiadiazecan-6-one (25) seemed to be remained in the brain.

As confirmed from the above results, the present invention provides new ligands for $^{99m}$Tc-labeled compounds to allow imaging of serotonergic nervous system of the brain by coupling N$_2$S$_2$ ligand with a proper antagonist capable of binding to serotonin receptor among the cranial nervous system.

Serotonin receptor imaging composition of arylpiperazine derivatives for imaging the cranial nervous system according to the present invention has no problem of amide hydrolysis in metabolism, has a high affinity for serotonin receptors, and can be labeled with an optimum radionuclide of technetium, thereby being usefully applied for monitoring neurodegenerative diseases or neurological diseases.

Microwave irradiation method for the preparation of radioactive isotope-labeled arylpiperazine derivatives can reach reaction temperature simply and more rapidly, and synthesize the desired compounds in higher yield than conventional heating methods.

The invention claimed is:

1. An arylpiperazine derivative represented by the following Chemical Formula 1:

[Chemical Formula 1]

wherein, X, Y, and Z are selected from the group consisting of (a), (b), (c), (d), and (e):
(a) X, Y, Z=H, C(OCH$_3$), CH;
(b) X, Y, Z=OCH$_3$, CH, CH;
(c) X, Y, Z=H, C(Cl), CH;
(d) X, Y, Z=H, N, CH;
(e) X, Y, Z=H, N, N; and
Ch is a chelating ligand selected from the group consisting of wherein
R is selected from the group consisting of:
—CH$_3$, —C$_2$H$_5$, —C$_3$H$_7$ and —C$_4$H$_9$.

2. The arylpiperazine derivative of claim 1, wherein the arylpiperazine derivative is further labeled with a radionuclide that forms a complex with the chelating ligand.

3. The arylpiperazine derivative of claim 2, wherein the radionuclide is $^{99m}$Tc.

4. A method for preparing a radionuclide complex of the arylpiperazine derivative of claim 1 comprising, labeling the arylpiperazine derivative of claim 1 with technetium, under microwave irradiation, in the presence of pertechnetate ion, using tetrahydroborate exchange resin as a reducing agent.

5. A radiopharmaceutical kit for the preparation of radiopharmaceutical drugs comprising a sealed, sterilized, non-pyrogenic vial containing the arylpiperazine derivative of claim 1 and a reducing agent.

6. The radiopharmaceutical kit of claim 5, wherein the reducing agent is tetrahydroborate exchange resin.

7. A radionuclide complex, comprising the arylpiperazine derivative of claim 1 and a radionuclide, wherein the radionuclide forms a complex with a chelating ligand of the the arylpiperazine derivative of claim 1.

8. The radionuclide complex according to claim 7, wherein the radionuclide is selected from the group consisting of $^{99}$Tc, $^{99m}$Tc, $^{188}$Re and $^{186}$Re.

9. The radionuclide complex according to claim 7, wherein the radionuclide is $^{99m}$Tc.

10. The radiopharmaceutical kit according to claim 5, wherein the arylpiperazine derivative and the reducing agent are in a lyophilized form.

11. A radiopharmaceutical composition comprising the radionuclide complex of claim 9 and a pharmaceutical carrier.

12. The radiopharmaceutical composition according to claim 11, wherein the pharmaceutical carrier is a saline.

13. A radiopharmaceutical composition comprising the radionuclide complex of claim 9 and a pharmaceutical carrier.

14. A method for preparing the arylpiperazine derivatives of claim 1 comprising:
(i) synthesizing a compound of Chemical Formula 13 under microwave irradiation,

[Chemical Formula 13]

wherein, X, Y, and Z are as defined in claim 1;
(ii) synthesizing a chelating ligand compound selected from the group consisting of Chemical Formulas 2-5 separately,

[Chemical Formula 2]

[Chemical Formula 3]

[Chemical Formula 4]

and

[Chemical Formula 5]

wherein, X' is Cl, Br, or I; and
(iii) synthesizing the arylpiperazine derivative of claim 1 by coupling the compound of Chemical Formula 13 obtained from step (i) with the chelating ligand obtained from step (ii) under microwave irradiation.

15. The method of claim 14, wherein the compound of Chemical Formula 13 is prepared by:
(i) reacting 2-aminopyridine with chloroacetyl chloride to form a compound of Chemical Formula 11,

[Chemical Formula 11]

(ii) reacting the compound of Chemical Formula 11 obtained from step (i) with an arylalkylpiperazine having a Chemical Formula of, wherein, X, Y, and Z are as defined in claim 1, to form a compound of Chemical Formula 12 under microwave irradiation or in the presence of a base,

[Chemical Formula 12]

; and (iii) reacting the compound of Chemical Formula 12 obtained from step (ii) with a reducing agent to form a compound of Chemical Formula 13,

[Chemical Formula 13]

16. A method for detecting serotonin receptor density, comprising the steps of:
adding the radionuclide complex of claim 9 into a pharmaceutical carrier;
injecting the carrier to a mammal; and
scanning the mammal by using a radioactive diagnostic imaging equipment.

17. A method for monitoring cranial nerve diseases of a mammal, comprising the steps of:
adding the radionuclide complex of claim 9 into a pharmaceutical carrier;
injecting the carrier to a mammal; and
scanning the mammal by using a radioactive diagnostic imaging equipment.

* * * * *